(12) United States Patent
Sin et al.

(10) Patent No.: US 8,282,961 B2
(45) Date of Patent: Oct. 9, 2012

(54) METHOD OF PREPARING A MICROCAPSULE CONTAINING UNSATURATED FATTY ACIDS, THE MICROCAPSULE PREPARED BY THE METHOD, AND ARTICLES CONTAINING THE MICROCAPSULE

(75) Inventors: Hong-Sig Sin, Jeonju-si (KR); Si-Ho Park, Jeonju-si (KR); Soo-Jong Um, Seongnam-si (KR); Jong-Hyun Lee, Jeonju-si (KR); Hee-Jeong Kim, Jeongju-si (KR); Ha-Lyong Jin, Iksan-si (KR); Hyoung-Su Kim, Jeonju-si (KR)

(73) Assignee: Chebigen Inc., Jeonju-Shi (KR)

( * ) Notice: Subject to any disclaimer, the term of this patent is extended or adjusted under 35 U.S.C. 154(b) by 760 days.

(21) Appl. No.: 12/377,506

(22) PCT Filed: Jul. 27, 2007

(86) PCT No.: PCT/KR2007/003623
§ 371 (c)(1),
(2), (4) Date: Jul. 10, 2009

(87) PCT Pub. No.: WO2008/020680
PCT Pub. Date: Feb. 21, 2008

(65) Prior Publication Data
US 2010/0080851 A1    Apr. 1, 2010

(30) Foreign Application Priority Data

Aug. 16, 2006  (KR) .......................... 10-2006-0076966

(51) Int. Cl.
*A61K 9/14* (2006.01)

(52) U.S. Cl. ........................................ 424/490; 424/496
(58) Field of Classification Search .................. None
See application file for complete search history.

(56) References Cited

U.S. PATENT DOCUMENTS

| | | | | |
|---|---|---|---|---|
| 6,444,242 B1 * | 9/2002 | Skelbaek et al. | ................ | 426/98 |
| 6,482,433 B1 * | 11/2002 | DeRoos et al. | ................ | 424/464 |
| 7,838,666 B2 * | 11/2010 | Yaginuma et al. | .............. | 536/56 |

FOREIGN PATENT DOCUMENTS

| | | |
|---|---|---|
| JP | 61126016 A | 6/1986 |
| JP | 05292899 A | 11/1993 |
| KR | 1020030063019 A | 7/2003 |

\* cited by examiner

*Primary Examiner* — David J Blanchard
*Assistant Examiner* — Tigabu Kassa
(74) *Attorney, Agent, or Firm* — Rothwell, Figg, Ernst & Manbeck, P.C.

(57) ABSTRACT

The present invention provides a preparing method of microcapsule containing unsaturated fatty acid comprising the steps of (a) preparing a first coating material by mixing and gelatinating one or more gums selected from the group consisting of xanthan gum, guar gum, and locusbean gum, with poly glycerin esters of fatty acid in sterilized water, adding unsaturated fatty acid to the solution, and homogenizing the solution; (b) preparing a second coating material by mixing and gelatinating starch or modified starch, gelatin or casein, and poly glycerin esters of fatty acid in sterilized water, adding the first coating material prepared in (a) to the solution, and homogenizing the solution; and (c) spraying the second coating material prepared in (b) in cold sterilized water; a microcapsule prepared by the method; and articles containing the microcapsule.

The present microcapsule has effects of preventing the oxidation of unsaturated fatty acid and inhibiting offensive smell.

5 Claims, 5 Drawing Sheets dsCHROM File Name: 02.11-1PELL.ddf
Analysis Name: [ANALYSIS] CBG-C2
Peak Width: 10(Points)
Peak Threshold: 50(uV)
Plot Attenuation: $7(2^{\wedge}n)$
Date: November 18, 14:55:00
Comment: November 1, 2002, 18:21:35/1

METHOD OF PREPARING A MICROCAPSULE CONTAINING UNSATURATED FATTY ACIDS, THE MICROCAPSULE PREPARED BY THE METHOD, AND ARTICLES CONTAINING THE MICROCAPSULE

CROSS REFERENCE TO RELATED APPLICATIONS

This application is a 35 U.S.C. §371 National Phase Entry Application from PCT/KR2007/003623, filed Jul. 27, 2007, and designating the United States, which claims priority under 35 U.S.C. §119 to Korean Patent Application No. 10-2006-0076966 filed Aug. 16, 2006, which is incorporated herein in its entirety.

TECHNICAL FIELD

The present invention relates to a preparing method of microcapsule containing unsaturated fatty acids, a microcapsule prepared by the method, and articles containing the microcapsule.

BACKGROUND ART

Unsaturated fatty acid is a fatty acid containing one or more double bonds, and mostly is liquid at room temperature. Highly unsaturated fatty acid generally indicates a fatty acid containing four or more double bonds per molecule, and recently, many physiological functions thereof have been reported. Particularly, an omega 3-fatty acid in unsaturated fatty acids exists in nerve cell membrane and retina, and plays a role to rapidly transfer electric stimulus from a cell membrane to another cell. It has been reported that an omega 3-fatty acid has an effect to protect cells in body, keep the structure of cells, and help the metabolism smoothly. Also, it has been reported that an omega 3-fatty acid is effective for inhibiting formation of membrane of blood, and stimulating formation of bones and strengthening bones at the same time.

As the kinds of omega 3-fatty acid, there are docosahexaenoic acid (DHA), Eicosapentaenoic acid (EPA), Docosapentaenoic acid (DPA), etc. Particularly, EPA increases the fluidity of blood to inhibit formation of thrombus and to decrease cholesterol value in blood that is the cause of arteriosclerosis. Clinical tests to EPA refined from fish oil showed that increase of EPA in blood results in decreasing cholesterols in blood and inhibiting agglutinations of platelet.

Also, it has been reported that EPA is effective for the prevention and treatment of atopic dermatitis, bronchial asthma, and allergic disease such as pollen allergy, and for the treatment of inflammatory disease such as chronic arthritis.

DPA is known as noticeable next generation material, and also known to be more effective for circulatory system diseases than DHA or EPA. It was confirmed in animal tests that DPA inhibits the receptor of vascular endothelial growth factor, KDR. Thus, medical centers have noted DPA for inhibition of vascularity. Also, DPA has been developed for the treatment of metabolic diseases because it is effective for emigration of vascular endothelial, inhibition of formation of thrombus, and metabolism of carbohydrate.

Omega 3-fatty acids are encouraged to take 0.6~1 g per day, and contained in fish oil, plankton, marine products, bean oil, mother's milk, etc. Particularly, more amounts of omega 3-fatty acids are required for newborn baby and young people for normal development of tissues. Recently, omega 3-fatty acid has received a huge attention because it is known that its deficiency may cause depression, schizophrenia, attention-deficit hyperactivity disorder, vision decline, cardiac disease, etc., and may aggravate stress.

But, unsaturated fatty acids are easily oxidized by oxygen or light. Particularly, highly unsaturated fatty acids are oxidized during storage, to emit unique fishy smell. To improve this problem, many studies for capsulation of unsaturated fatty acids have been conducted.

In capsulating unsaturated fatty acids, capsule material should have excellent film forming ability to protect unsaturated fatty acids and low viscosity of emulsion. And, unsaturated fatty acids in capsules have to be dispersed uniformly and finely in emulsion state.

In the case of puverization of capsule, the efficiency of microcapsulation depends on the form of used capsule material, and is the most important element to affect the emulsion's stableness before drying, the physical stableness after drying, and the storage term. And, capsule materials affect solubility, emulsification, membrane formation, and drying property. Thus, capsule materials used for pulverization of unsaturated fatty acids such as omega 3-fatty acids are very limited.

And, the degree of capsulation of unsaturated fatty acids depends on physical property of unsaturated fatty acids, and the property and state of unsaturated fatty acids depend on combination method and combination rate in functional foods. Thus, there are many difficulties in applying capsules of containing unsaturated fatty acids to articles.

Also, it has been needed to pulverize capsulated unsaturated fatty acids in order to apply unsaturated fatty acids having many merits as above described, to various products.

Capsulating methods of highly unsaturated fatty acids for utilizing the merits of capsule have been reported. For example, Noh et al. (Korean Patent Publication No. 2000-0038444) disclosed a method to improve physiological property of fish oil by a capsulating method of highly unsaturated fatty acids such as DHA (docosahexaenoic acid), through using polysaccharide like glutinous rice starch, and emulsifying agents like twin series. But, this method has disadvantages that the dispersibility of fish oil cannot be maintained in water solution for a long time, and the heat stability (20° C.) is lowered.

Park et al. (Korean Patent Publication No. 2004-0042987) disclosed a method of capsulating fish oil containing highly unsaturated fatty acids by using soy protein, a protein kind of coating material, etc., applicable to many fields including food, but the unstability of capsule is a disadvantage of the method.

Also, many soft capsules containing highly unsaturated fatty acids have been developed. But, soft capsules give an image like medicine in oral administration, and so are offensive, particularly for children. Thus, there have been many studies about tablet form of unsaturated fatty acids from the point of industries and users, but no clear solutions have appeared yet.

DISCLOSURE OF INVENTION

Technical Problem

The present invention is to provide a preparing method of microcapsule containing unsaturated fatty acids, having more improved dispersion and stability than previous microcapsules containing unsaturated fatty acids, a microcapsule prepared by the method, and articles containing the microcapsules.

Technical Solution

The present preparing method of microcapsule containing unsaturated fatty acids comprises the steps of, (a) preparing a first coating material by mixing and gelatinating one or more gums selected from the group consisting of xanthan gum, guar gum, and locust bean gum, with poly glycerin esters of fatty acid in sterilized water, adding unsaturated fatty acids to the mixture, and homogenizing the mixture; (b) preparing a second coating material by mixing and gelatinating starch or modified starch, gelatin or casein, and poly glycerin esters of fatty acid in sterilized water, adding the first coating material of (a) to the mixture, and homogenizing the mixture; and (c) spraying the second coating material prepared in (b) in cold sterilized water.

In the present method, preferably, unsaturated fatty acid is arachidonic acid, docosahexaenoic acid (DHA), Eicosapentaenoic acid (EPA), Docosapentaenoic acid (DPA), or Conjugated linolenic acid (CLA).

Preferably, the unsaturated fatty acids of step (a) in the present method are used by 2.0~10% (w/w) based on a total weight of the microcapsule. In this range, the microcapsule has the best effect in the yield, dispersion and stability.

Preferably, poly glycerin esters of fatty acids of step (a) in the present method are used by 0.3~1.0% (w/w) based on a total weight of the microcapsule, and the gums of step (a) are used by 0.1~3.0% (w/w) based on a total weight of the microcapsule. In these ranges, oxidation to cause fishy smell of unsaturated fatty acids can be inhibited.

Preferably, the starch or modified starch of step (b) in the present method is used by 1~2.00% (w/w) based on a total weight of the microcapsule, the gelatin or casein of step (b) is used by 0.5~20.0% (w/w) based on a total weight of the microcapsule, and poly glycerin esters of fatty acid of step (b) are used by 0.1~1.5% (w/w) based on a total weight of the microcapsule. In these ranges, the combination ratio of second coating material and first coating material is proper.

Preferably, the homogenizing temperatures of steps (a) and (b) in the present method are 30° C.~50° C. more preferably 35° C.~45° C., most preferably 40° C. If the homogenizing temperature is over 50° C., unsaturated fatty acids' physical properties may be changed to cause oxidation. If the temperature is below 30° C., the coating material is hardened to decrease the stability of capsule. Approximately 40° C. is an appropriate temperature to maintain the uniform gelatification of best core material and coating materials, and is the best condition to inhibit oxidation of unsaturated fatty acids.

The present invention also provides microcapsules containing unsaturated fatty acids prepared by the above method.

Also, the present invention provides articles containing the microcapsules containing unsaturated fatty acids prepared by the above method. The articles include fermented milk, processed milk, fermented foods such as Korean hot pepper paste, Korean soybean paste, Kimchi, functional drinks, functional foods, general foods, medicine, and cosmetics.

Moreover, the present invention provides a powder containing the microcapsules containing unsaturated fatty acids prepared by the above method. The powder can be prepared by microcapsule preparing methods known in the art. In case of realizing the powder prepared according to the present invention by dissolving in water, it is converted to a liquid capsule. The size of the realized liquid capsule is 300~600 nm, which is less than 1.5~17 μm that is the size of the microcapsule according to the present invention, because water in the capsule is discharged out if the capsule is powdered.

Further, the present invention provides tablets prepared by using the powder according to the present invention.

ADVANTAGEOUS EFFECTS

The microcapsules containing unsaturated fatty acid according to the present invention have an effect to be maintained stably without offensive smell when stored at 4° C. for one or more months after it is prepared. And, the present microcapsules have effects that the yield of the effective ingredient is more than 95%, and the dispersibility can be maintained in water solution even for a long time of storage.

The present microcapsule can prevent unique smell of rotten fish from oxidization of unsaturated fatty acids. Thus, various stable forms of formulations such as powder, tablet, etc. can be provided with maintaining the functionality of unsaturated fatty acids, depending on the types and uses of articles. Also, the present microcapsules have an effect to release unsaturated fatty acids according to the heat and retention time in body after they arrive at the intestine that is the destination in the body.

MODE FOR INVENTION

The following examples are intended to further illustrate the present invention, and the scope of the present invention is not intended to be limited thereby in any way.

Example 1

Preparation of CLA (Conjugated Linoleic Acid) Microcapsule

Xanthan gum (Sigma) of 1.5 g, poly glycerin esters of fatty acids (Ilshinwells Co., Ltd, Almax 9060) of 0.5 g and locust bean gum (Sigma) of 0.1 g were mixed with sterile water of 50 g in a gelatification bowl. And, the solution was gelatificated at 120° C. for 5 min, and was cooled to 60° C. Then, CLA (95%, Lipozen) of 6.3 g (w/w) was added to the solution, and homogenized at 6,400 rpm and 40° C. (Water Bath, VISION) for 5 min by a homogenizer (IKA T-50) to obtain a first coating material.

Modified starch (LOSTAR, Cornproducts Korea Inc.) of 0.3 g and gelatin (SAMMI INDUSTRIAL CO., LTD) of 3.0 g, poly glycerin esters of fatty acids (Almax 9080) of 0.5 g, and sterile water of 100 g were mixed in a gelatification bowl, and gelatificated at 120° C. for 5 min. And, the solution was cooled to 40° C., and the first coating material was added to the solution. After that, the solution was homogenized at 6,400 rpm, for 5 min by a homogenizer (IKA T-50) to obtain a second coating material. The second coating material of 827 g was sprayed directly in sterilized cool water to prepare a CLA microcapsule.

※ Properties of CLA Microcapsule

TABLE 1

| Capsule form | Content of CLA[1] | Color[2] | Physical property[3] | Offensive smell[4] | Size[5] | Yield[6] |
|---|---|---|---|---|---|---|
| CLA microcapsule | 4.45% (w/w) | White liquid | Stable at below 30° C. and pH 1.0~7.1 | Not detected | 1.5~1.7 μm | 95.0% |

In Table 1, the
[1] content of CLA was measured by the Experimental Example 1 below,
[2] the color was observed visually,
[3] the physical property was measured by the Experimental Example 2 below,
[4] the offensive smell was measured by a sensory test,
[5] the size was measured by the Experimental Example 3 below, and
[6] the yield is 95% of average raw material output to the total weight of raw materials.

Experimental Example 1

CLA Analysis

The content of CLA in CLA microcapsule was measured by GC analysis method, as follows.

Figure 1:
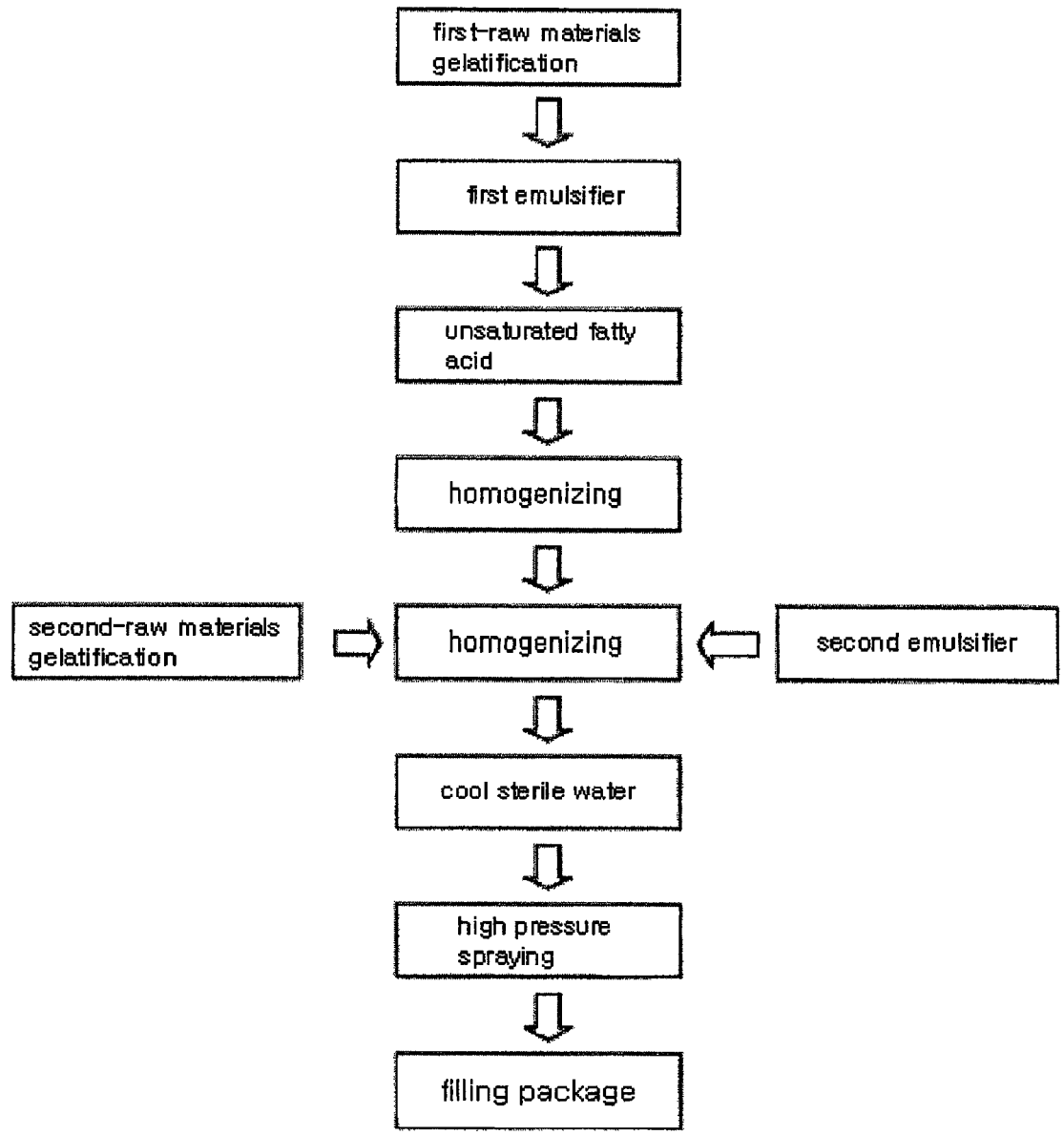
FIG. 1 represents a scheme of the preparing method of the microcapsules containing unsaturated fatty acids according to the present invention.
Figure 2:
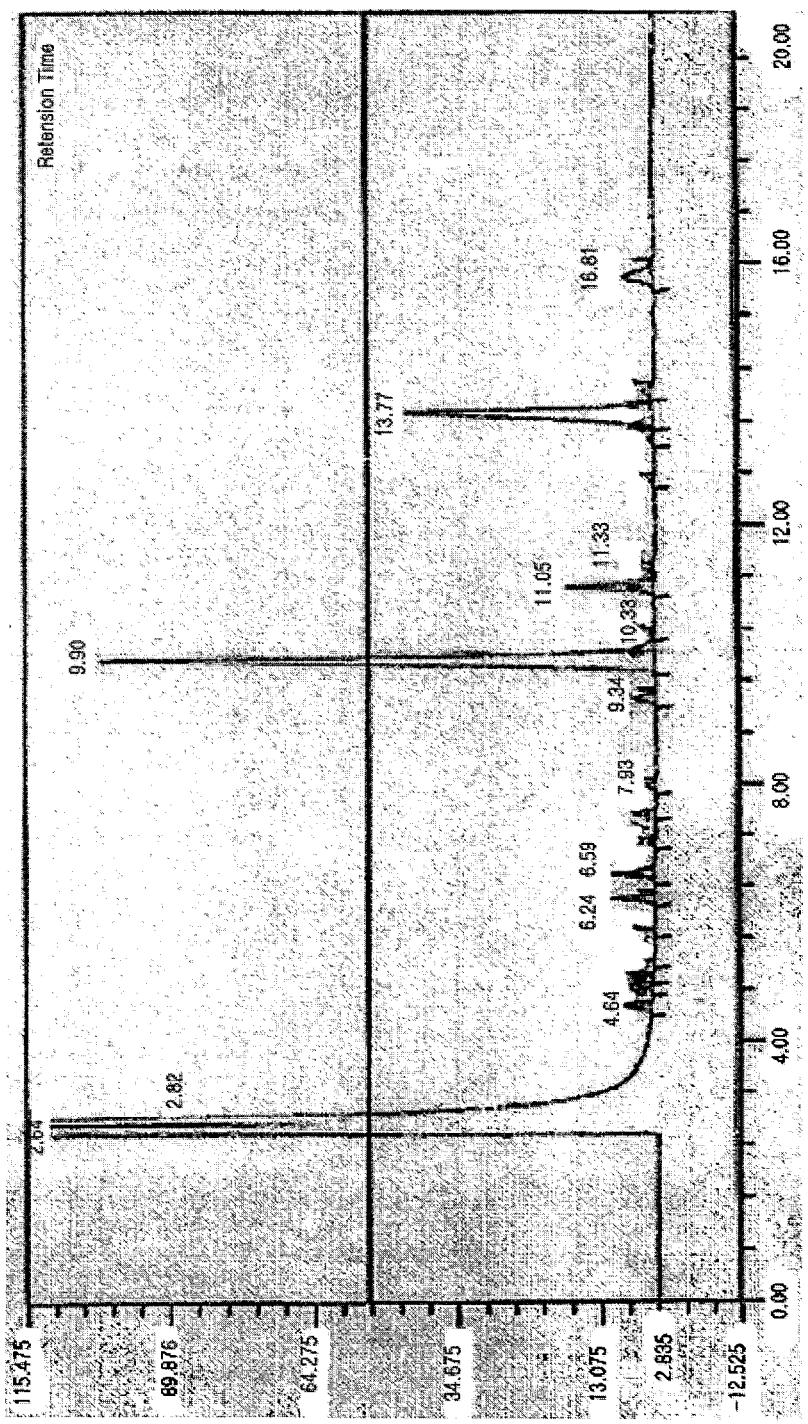
FIG. 2 represents values of CLA content of CLA microcapsule prepared in Example 1.

CLA microcapsules were broken in an incubator for 5 hr. After that, they were kept at cooling condition, and centrifuged at 9000 rpm and 4° C. for 7 min, to obtain a supernatant. Isopropyl alcohol was added to the supernatant, and the mixture was stirred for 5 min. And, hexane was added to the supernatant, and the mixture was stirred for 5 min, and left for 10 min. Then, only the supernatant was separated therefrom again, and distillated under reduced pressure at 45~50° C. And, 1N NaOH/MeOH was added to the supernatant, and suspended. After that, the suspension solution was heated at 100° C. for 10 min, and added to $BF_3$/MeOH to be methylated. And, hexane was added to the suspension solution, and heated at 100° C. for 1 min to obtain methylated CLA(CLA-OMe), from which the content of CLA in the microcapsule was calculated by GC (Varian CP-3800) analysis, to be 4.45% (the retention time was 13.77 min) (see, FIG. 2).

Experimental Example 2

Test of pH Stability and Dispersibility

The pH stability and dispersibility of the microcapsule (liquid form) containing unsaturated fatty acid, prepared in the Example 1, were measured by time after pH titrating by using Trizma-base buffer (20 mM Triz/100 mM NaCl), and 0.1N HCl & 0.1N NaOH, at 37° C. The result was represented in the following Table 2.

TABLE 2

| | Time | | | | | | | |
|---|---|---|---|---|---|---|---|---|
| Ph | 15 min | 30 min | 45 min | 1 hr | 1 hr 15 min | 1 hr 30 min | 2 hr | 2 hr 30 min |
| 1.04 | stable | Stable | stable | Stable | stable | stable | stable | Released slowly |
| 2.10 | stable | Stable | stable | Stable | stable | stable | stable | Released slowly |
| 3.00 | stable | Stable | stable | Stable | stable | stable | stable | Released slowly |
| 4.11 | stable | Stable | stable | Stable | stable | stable | stable | Released slowly |
| 5.52 | stable | Stable | stable | Stable | stable | stable | stable | Released slowly |
| 7.10 | stable | Stable | stable | Stable | stable | stable | stable | Released slowly |
| 8.13 | Coagulation | Coagulation | Coagulation | Coagulation | Coagulation | Coagulation | Coagulation | Coagulation |
| 9.50 | Coagulation | Coagulation | Coagulation | Coagulation | Coagulation | Coagulation | Coagulation | Coagulation |

The microcapsule of the present invention has good stability and dispersibility for 2 hr at acidic and neutral condition. But, the stability of the microcapsule decreased rapidly after 2 hr. And, the dispersibility of the microcapsule was poor at alkali condition.

Experimental Example 3

Size of the Microcapsule

The size of the microcapsule containing unsaturated fatty acid, prepared in the Example 1, was measured by ELS (Electrophoretic Light Scattering System, Ostuka Ltd, ELS-8000) after diluting the microcapsule to 250 times by sterilized third distilled water. As a result, the average size of microcapsule was 1,500 nm to 1,700 nm.

Example 2

Preparation of Powder of CLA (Conjugated Linoleic Acid) Microcapsule

The powder of CLA microcapsule was prepared as follows.
Low fat powdered skim milk (Dongwon Dairy Food Co., Ltd.) of 25.55 g and Maltodextrin (MAX-1000, Archer Daniels Midland company, USA) of 3.48 g were dissolved in water of 50° C., mixed with the CLA microcapsule [CLA content: 4.45% (w/w)] of 70.97 g prepared in the Example 1, and homogenized by a homogenizer (APV Rannie 5; Pressure=100 bar). After that, the mixture was put in a container of 900 ml for lyophilization, frozen at −63° C. for 12 h or more, lyophilized by a lyophilizer (Ilshin, Model No: FD5512; Starting temperature: −43° C., and Final temperature: 30° C.) under inner vacuum pressure of 7 mTorr for 72 hour, pulverized, and filtered by a sieve plate of 150 mesh, to obtain a powder.

※ Properties of the Powder of CLA Microcapsule

TABLE 3

| Capsule form | Content of CLA[1] | Color[2] | Offensive smell[3] | Size of particle[4] | Recovery rate of powder[5] |
|---|---|---|---|---|---|
| Powder of CLA microcapsule | 13.1% (w/w) | White powder | Faint taste of powdered skim milk | Below 150 mesh | 31.9% |

In Table 3,
[1]the content of CLA was measured by the same method as the Experimental Example 1,
[2]the color was observed visually,
[3]the offensive smell was measured by a sensory test,
[4]the size of particle was from filtering with a sieve plate of 150 mesh, and
[5]the recovery rate of powder is 90% of average raw material output to the total weight contents of raw materials.

Example 3

Preparation of the Tablet of CLA (Conjugated Linoleic Acid) Microcapsule

Figure 3:
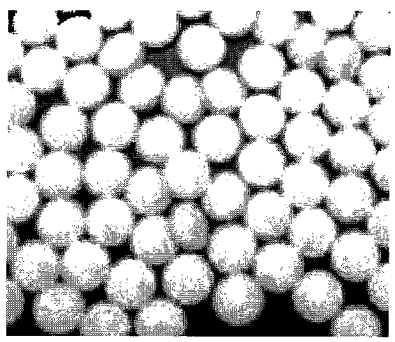
FIG. 3 represents a photo of a tablet containing CLA microcapsule prepared in Example 3.

The powder of CLA microcapsule (CLA content: 13.1%) of 100 g prepared in the Example 2, and milk calcium (SUNG POONG PRODUCTS) of 100 g were mixed homogeneously, and a tablet was prepared by a tablet-making machine (SEJONG Pharmatech Co., Ltd, SH-28, Feed Rate=280,000 tablet/hr). FIG. 3 is a photo of such prepared tablet of CLA microcapsule.

※ Properties of the Tablet of CLA Microcapsule

TABLE 5

| Capsule form | Content of CLA[1] | Color[2] | Offensive smell[3] | Size of tablet[4] |
|---|---|---|---|---|
| Tablet of CLA microcapsule | 6.55% (w/w) | White tablet | Faint smell of lactic acid calcium | Φ = 8 mm, D = 3 mm |

In Table 5,
[1]the content of CLA was measured by the method of the Experimental Example 1,
[2]the color was observed visually,
[3]the offensive smell was measured by a sensory test,
[4]and the size of tablet was measured, based on the casting size of tablet shape.

Example 4

Preparation of Omega-3 Fatty Acid Microcapsule

Xanthan gum (Sigma) of 1.5 g, poly glycerin esters of fatty acids (Ilshinwells Co., Ltd, Almax 9060) of 0.5 g, and locust bean gum (Sigma) of 0.5 g were mixed with sterilized water of 50 g in a gelatification bowl. And, the solution was gelatificated at 120° C. for 5 min, and was cooled by 60° C. And, omega-3-fatty acid (containing DHA of 40%, EPA of 10%, and Lipozen) of 3.0 g was added to the solution, homogenized at 6,400 rpm, cooled to 40° C. (the temperature is important to prevent the oxidation of omega-3-fatty acid) (Water Bath, VISION) for 5 min by a homogenizer (IKA T-50) to obtain a first coating material.

Modified starch (LOSTAR, Cornproducts Korea Inc.) of 1.1 g and gelatin (Sammi Industrial Co., LTD) of 14.5 g, poly glycerin esters of fatty acids (Almax 9080) of 0.9 g, and sterilized water of 100 g were mixed in a gelatification bowl, and gelatificated at 120° C. for 5 min. And, the solution was cooled to 40° C., and the first coating material was added to the solution. After that, the solution was homogenized at 6,400 rpm, for 5 min by a homogenizer (IKA T-50) to obtain a second coating material. The second coating material of 828

TABLE 4

| | Ratio of solubility | Solubility[1] | Solubility rate | Remainder[2] | Size of capsule[3] |
|---|---|---|---|---|---|
| Powder of CLA microcapsule | 1 g/10 mL H$_2$O | 0.87 g/mL | 87% | 0.127 g | Average 477 nm |

In Table 4,
[1]the solubility was measured in water of 25° C.,
[2]the remainder was a weight after the remainder filtered by a filter paper (Whatmann No. 2) was dried in a drying machine at 100° C. for 5 hr,
[3]the size of capsule was an average of values measured twice by ELS (Electrophoretic Light Scattering System, Ostuka Ltd, ELS-8000) after the powder of CLA microcapsule was converted to liquid by diluting the microcapsule to 250 times with sterilized third distilled water.

g was sprayed directly in sterilized cool water, to prepare an omega-3-fatty acid microcapsule.

※ Properties of Omega-3-fatty Acid Microcapsule

TABLE 6

| Capsule form | Content of omega-3-fatty acid[1] | Color[2] | Physical property[3] | Degree of offensive smell[4] | Size[5] | Yield[6] |
| --- | --- | --- | --- | --- | --- | --- |
| Omega-3-fatty acid microcapsule | DHA 1.2% (w/w) EPA 0.3% (w/w) | White liquid | Stable below 30° C. and at pH 1.0~7.1 | 0.3 ppm | 1.5~1.7 μm | 95.0% |

In Table 6,

[1] the content of omega-3-fatty acid was measured by the method of the Experimental Example 1,

[2] the color was observed visually,

[3] the physical property was measured by the method of the Experimental Example 2,

[4] the degree of offensive smell was measured by the method of the Experimental Example 4 below,

[5] the size was measured by the method of the Experimental Example 3, and

[6] the yield is 95% of average raw material output to the total weight of raw materials.

Experimental Example 4

Offensive Smell of omega-3-fatty Acid Microcapsule

Each maximum ppm of offensive smell of omega-3-fatty acid, omega-3-fatty acid microcapsule prepared by the Example 4, a milk, and a milk containing 2% of omega-3-fatty acid microcapsule was measured by using PHC (Perkin-Elmer PHOTOVAC-microFid EEX) measuring machine for 1 min.

The results are shown in Table 7 below (the internal standard analysis was measured based on methane of 300 ppm, and the point that the amount of offensive smell generated from the milk suddenly changes is when the decay is begun).

TABLE 7

| Analysis sample (storing at 4° C.) | Omega-3-fatty acid (36%) | Omega-3-fatty acid microcapsule | Milk (on the market) | Milk containing 2% of omega-3-fatty acid microcapsule |
| --- | --- | --- | --- | --- |
| The measured value (ppm) | 5.4 | 0.3 | 0.0 | 0.0 |

Figure 4:
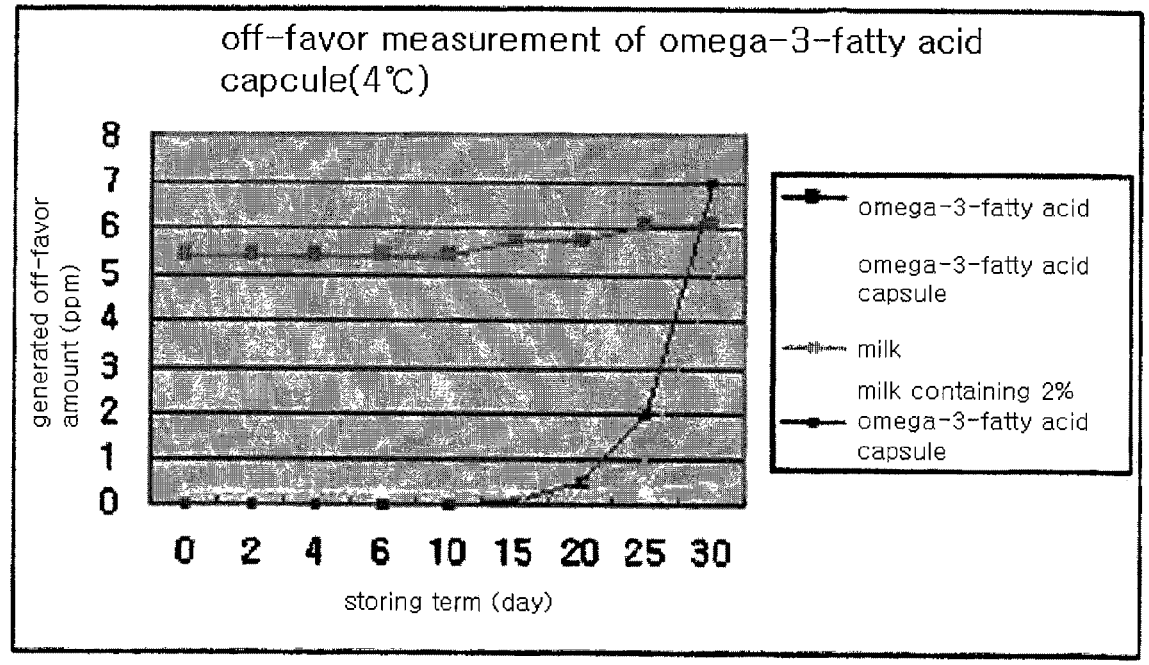
FIG. 4 represents values of the degree of offensive smell when the microcapsules containing omega 3 fatty acid prepared in. Example 4 were stored at 4° C.

And, the offensive smell of each sample was measured during the storage of 4° C. and 25° C. for 30 days by PHC (Perkin-Elmer PHOTOVAC-microFid EEX) measuring machine. The results were represented in FIG. 4 and FIG. 5. The degree of offensive smell of omega-3-fatty acid microcapsule at 4° C. even after 30 days was below 1 ppm (see, FIG. 4). This shows that the omega-3-fatty acid microcapsule of the present invention has excellent inhibitive ability to offensive smell than the other samples (Omega-3-fatty acid, milk, and milk containing 2% omega-3-fatty acid microcapsule).

Figure 5:
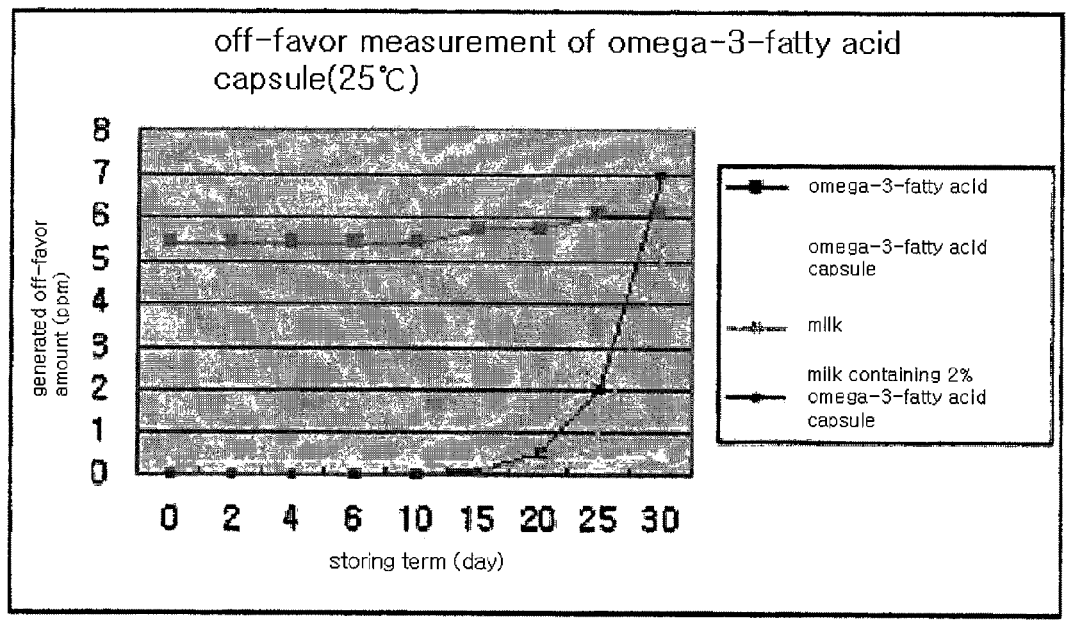
FIG. 5 represents values of the degree of offensive smell when the microcapsules containing omega 3 fatty acid prepared in. Example 4 were stored at 25° C.

And, even when the omega-3-fatty acid microcapsule of the present invention was kept at 25° C. for 30 days, the degree of offensive smell was below 5 ppm, which shows that it has excellent inhibitive ability (see, FIG. 5).

Experimental Example 5

Oxidation Test of Omega-3-fatty Acid Microcapsule

Figure 6:
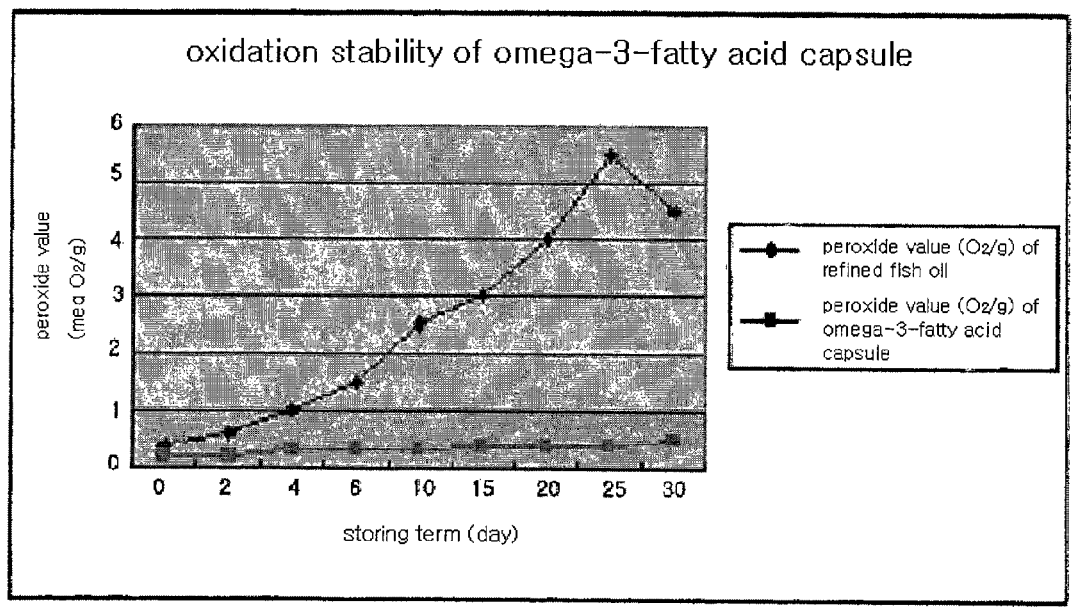
FIG. 6 represents values of peroxide values when the microcapsules containing omega 3 fatty acid prepared in Example 4 were stored at 27° C. for 30 days.

The omega-3-fatty acid microcapsule prepared in the Example 4, 20 ml and a refined fish-oil (the content of omega-3-fatty acid is 50%) of 20 ml each were put on petri dish separately, and exposed to air at room temperature (27° C.), and an oxidation test was conducted by using '③ the measuring method of peroxide value,' '(4) chemical test,' '4) Lipid,' General Test Method of KOREA FOOD CODE (Korea Foods Industry Association, 2004). The results were represented in FIG. 6. The peroxide value of the omega-3-fatty acid microcapsule of the present invention was below 1 meq $O_2$/g after 30 days.

Example 5

Preparation of the Powder of Omega-3-fatty Acid Microcapsule

The powder of omega-3-fatty acid microcapsule was prepared as follows.

Maltodextrin (MAX-1000, Archer Daniels Midland company, USA) of 5.0 g was dissolved in water at 50° C., mixed with the omega-3-fatty acid microcapsule of 95.0 g prepared in the Example 4, and homogenized by a homogenizer (APV Rannie 5, Pressure=150 bar). After that, it was added into a container for lyophilization (900 ml), frozen at −63° C. for 12 h or more, and lyophilized by a lyophilizer (Ilshin, Model No: FD5512; Starting temperature: −43° C., and Final temperature: 30° C.) under the inner pressure of 7 mTorr for 72 hour. And, it was pulverized, and filtered by a sieve plate of 150 mesh to obtain a powder.

※ Properties of the Powder of Omega-3-fatty Acid (31.35% (w/w)) Microcapsule

TABLE 8

| Capsule form | Content of omega-3-fatty acid[1] | Color[2] | Degree of offensive smell[3] | Size of particle[4] | Recovery rate of powder[5] |
|---|---|---|---|---|---|
| Powder of omega-3-fatty acid microcapsule | DHA 25.08% (w/w) EPA 6.27% (w/w) | White powder | 1.5 ppm | Below 150 mesh | 8.9% |

In Table 8,
[1] the content of omega-3-fatty acid was measured by the method of the Experimental Example 1,
[2] the color was observed visually,
[3] the degree of offensive smell was measured by the method of the Experimental Example 4,
[4] the size of particle was from filtering with a sieve of 150 mesh, and
[5] the recovery rate of powder is 90% of average raw material output to the total weight of raw materials.

Example 6

Preparation of the Powder of Omega-3-Fatty Acid (Content: 32.01%) Microcapsule The powder of omega-3-fatty acid [content: 32.01% (w/w)] microcapsule was prepared by the method of the Example 5 by using dextrin of 3.0% (w/w) and the omega-3-fatty acid microcapsule of 97.0% (w/w).

※ Properties of the Powder of Omega-3-fatty Acid [32.01% (w/w)] Microcapsule

TABLE 9

| Capsule form | Content of omega-3-fatty acid[1] | Color[2] | Degree of offensive smell[3] | Size of particle[4] | Recovery rate of powder[5] |
|---|---|---|---|---|---|
| Powder of omega-3-fatty acid microcapsule | DHA 25.61% (w/w) EPA 6.40% (w/w) | White powder | 1.5 ppm | Below 150 mesh | 7.4% |

In Table 9,
[1] the content of omega-3-fatty acid was measured by the method of the Experimental Example 1,
[2] the color was observed visually,
[3] the degree of offensive smell was measured by the method of the Experimental Example 4,
[4] the size of particle was from filtering with a sieve of 150 mesh, and
[5] the recovery rate of powder is 90% of average raw material output to the total weight of raw materials.

Example 7

Preparation of the Tablet of Omega-3-Fatty Acid (Content: 31.35%) Microcapsule The powder of omega-3-fatty acid microcapsule (the content of omega-3-fatty acid is 31.35%) of 100 g prepared in the Example 5, and milk calcium SP (SUNG POONG PRODUCTS) of 100 g were mixed homogeneously, and a tablet was prepared by using a tablet-making machine (SEJONG Pharmatech Co., Ltd, SH-28, Feed Rate=280,000 tablet/hr).

※ Liquid Conversion Rate of the Powder of Omega-3-fatty Acid (32.01% (w/w)) Microcapsule

TABLE 10

| | Ratio of solubility | Solubility[1] | Solubility rate | Remainder[2] | Size of capsule[3] |
|---|---|---|---|---|---|
| Powder of omega-3-fatty acid microcapsule | 1 g/10 mL H$_2$O | 0.95 g/mL | 95% | 0.048 g | Average 347 nm |

In Table 10,
[1] the solubility was measured in water of 25° C.,
[2] the remainder was a weight after the remainder filtered by a filter paper (Whatmann No. 2) was dried in a drying machine at 100° C. for 5 hr,
[3] the size of capsule was an average of values measured twice by ELS (Electrophoretic Light Scattering System, Ostuka Ltd, ELS-8000) after the powder of CLA microcapsule was converted to liquid form by diluting the microcapsule to 250 times by sterilized third distilled water.

The tablet of omega-3-fatty acid microcapsule (the content of omega-3-fatty acid is 32.01%) was prepared, but the defective rate of articles was high since the solidity of tablet was poor.

※ Properties of the Tablet of Omega-3-fatty Acid Microcapsule

TABLE 11

| Capsule form | Content of omega-3-fatty acid[1] | Color[2] | Offensive smell[3] | Size of tablet[4] |
|---|---|---|---|---|
| Tablet of omega-3-fatty acid microcapsule | 15.68% (w/w) | Faint yellow tablet | Faint taste of lactic acid calcium | φ = 8 mm, D = 3 mm |

Figure 7:
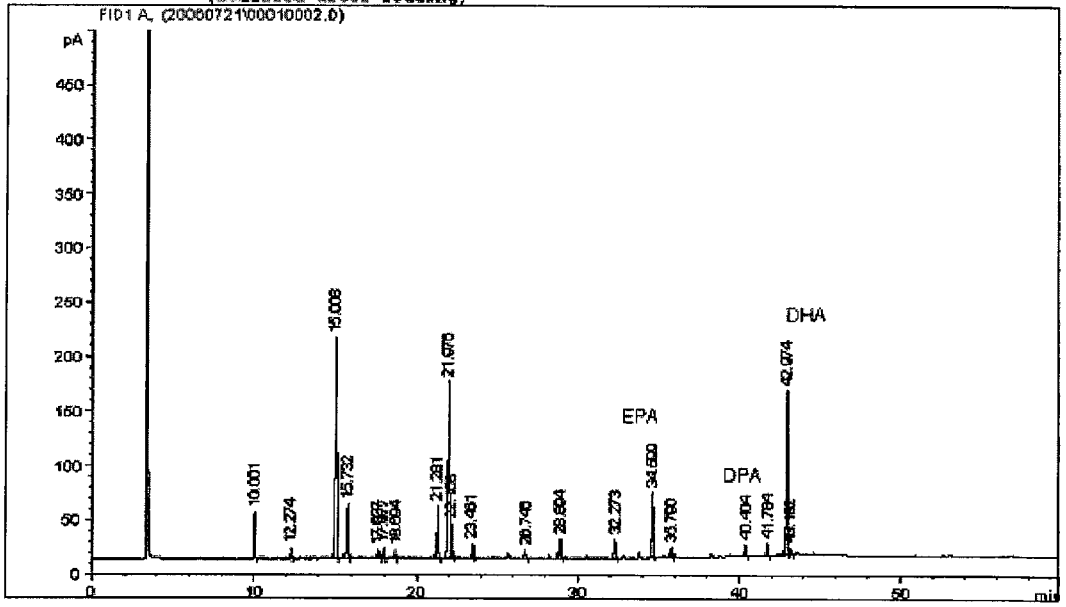
FIG. 7 represents values of the content of omega 3 fatty acid of a tablet containing the microcapsules of omega 3 fatty acid prepared in Example 7.

In Table 11,

[1] the content of omega-3-fatty acid was measured by the method of '① the qualitative and quantitative method by gas chromatography <The method No. 1; Varian CP-3800, FID>,' '(4) fatty acid,' '4) lipid,' of 'General test method of KOREA FOOD CODE (Korea Foods Industry Association, 2004).' And, the results were shown in FIG. 7 (the retention time: DHA - 42.074 min, EPA - 34.500 min, and DPA - 40.404 min). Each amount of DHA, EPA and DPA was measured by integrating the detected peak area.
[2] The color was observed visually,
[3] the offensive smell was measured by a sensory test,
[4] and the size of tablet was measured based on the casting size of tablet shape.

Example 8

Preparation of DPA Microcapsule

DPA microcapsule was prepared by using DPA (content: 7.0%, Japan LS corporation) 3.0% (w/w) by the method of the Example 4.

※ Properties of DPA Microcapsule

TABLE 12

| Capsule form | Content of DPA[1] | Color[2] | Physical property[3] | Degree of offensive smell[4] | Size[5] | Yield[6] |
|---|---|---|---|---|---|---|
| DPA microcapsule | DPA 0.21% (w/w) | Faint yellow liquid | Stable at below 30° C. and pH 1.0~7.1 | 3 ppm below | 1.5~1.7 μm | 95.0% |

In Table 12,

[1] the content of DPA was measured by the method of the Experimental Example 1,
[2] the color was observed visually,
[3] the physical property was measured by the method of the Experimental Example 2,
[4] the offensive smell was measured by the method of the Experimental Example 4,
[5] the size was measured by the method of the Experimental Example 3, and
[6] the yield is 95% of average raw material output to the total weight of raw materials.

INDUSTRIAL APPLICABILITY

The unsaturated fatty acid microcapsule of the present invention has an effect to be preserved stably without generating offensive smell during the storage at 4° C. for one or more months after the preparation. And, the yield of effective ingredient in the present microcapsule is more than 95%, and the microcapsule has an effect to maintain the dispersibility in water solution during the storage of a long period of time.

The microcapsule of the present invention maintains functionality of unsaturated fatty acid, and can provide various and stable formulations such as powder, tablet, etc., depending on types and uses of articles, because the present microcapsule can prevent generation of unique smell of decayed fish oil due to oxidation of unsaturated fatty acid. And, the present microcapsule has an effect to release the unsaturated fatty acid according to the heat and retention time in the body after it arrives at the intestine that is the destination in the body.

What is claimed is:

1. A preparing method of microcapsule containing unsaturated fatty acid comprising the steps of, (a) preparing a first coating material by mixing and gelatinating xanthan gum and locust bean gum, with poly glycerin esters of fatty acid in sterilized water; adding unsaturated fatty acid to the solution, and homogenizing the solution; (b) preparing a second coating material by mixing and gelatinating modified starch and gelatin, with poly glycerin esters of fatty acid in sterilized water; adding the first coating material prepared in (a) to the solution, and homogenizing the solution; and (c) spraying the second coating material prepared in (b) in cold sterilized water, wherein the unsaturated fatty acid is omega-3 fatty acid containing Docosahexaenoic acid (DHA) and Eicosapentaenoic acid (EPA).

2. The method of claim 1, wherein the unsaturated fatty acid of step (a) is used by 2.0-10% (w/w) based on a total weight of the microcapsule.

3. The method of claim 1, wherein poly glycerin esters of fatty acid of step (a) is used by 0.3-1.0% (w/w) based on a total weight of the microcapsule, and gums of step (a) is used by 0.1-3.0% (w/w) based on a total weight of the microcapsule.

4. The method of claim 1, wherein modified starch of step (b) is used by 0.01-2.00% (w/w) based on a total weight of the microcapsule; gelatin of step (b) is used by 0.5-20% (w/w) based on a total weight of the microcapsule; and poly glycerin esters of fatty acid of step (b) is used by 0.1-1.5% (w/w) based on a total weight of the microcapsule.

5. The method of claim 1, wherein the homogenizing temperatures of steps (a) and (b) step are 30° C.-50° C.

* * * * *